United States Patent [19]

Ogura et al.

[11] Patent Number: 4,575,257
[45] Date of Patent: Mar. 11, 1986

[54] THERMAL SHOCK CHAMBER

[75] Inventors: Toichi Ogura, Shiga; Ikuo Kanamori, Osaka; Keiichi Murano, Sakurai, all of Japan

[73] Assignee: Tabai Espec Corp., Japan

[21] Appl. No.: 585,191

[22] Filed: Mar. 1, 1984

[30] Foreign Application Priority Data

Oct. 5, 1983 [JP] Japan .................. 58-186179

[51] Int. Cl.⁴ .................. G01N 25/00; F25B 29/00
[52] U.S. Cl. .................. 374/45; 374/57; 165/27; 165/61; 126/285 B
[58] Field of Search .................. 374/10-12, 374/39, 45, 57; 73/432 SD; 126/285 B; 236/1 B, 13; 165/27, 61

[56] References Cited

U.S. PATENT DOCUMENTS

| | | | |
|---|---|---|---|
| 2,717,766 | 9/1955 | Becker | 165/61 |
| 4,156,454 | 5/1979 | Skala | 165/61 |
| 4,354,547 | 10/1982 | Sugiura | 165/27 |

FOREIGN PATENT DOCUMENTS

| | | | |
|---|---|---|---|
| 897760 | 11/1953 | Fed. Rep. of Germany | 374/45 |
| 2650686 | 5/1978 | Fed. Rep. of Germany | 374/45 |
| 1291724 | 3/1962 | France | 236/13 |
| 700820 | 12/1979 | U.S.S.R. | 374/45 |
| 838530 | 6/1981 | U.S.S.R. | 374/57 |
| 896509 | 1/1982 | U.S.S.R. | 374/57 |
| 953527 | 8/1982 | U.S.S.R. | 374/57 |

Primary Examiner—Charles E. Frankfort
Assistant Examiner—W. Morris Worth
Attorney, Agent, or Firm—Larson and Taylor

[57] ABSTRACT

A thermal shock chamber comprising a test area, a high-temperature air conditioning unit having a gas outlet and a gas inlet adjacent to the test area, an outside air supplying unit having an air outlet and an air inlet adjacent to the test area, a low-temperature air conditioning unit having a gas outlet and a gas inlet adjacent to the test area, a first damper assembly for opening the outlet and the inlet of one of the high-temperature air conditioning unit and the outside air supplying unit and closing the outlet and the inlet of the other unit at the same time, and a second damper assembly for opening the outlet and the inlet of one of the low-temperature air conditioning unit and the outside air supplying unit and closing the outlet and the inlet of the other unit at the same time.

4 Claims, 2 Drawing Figures

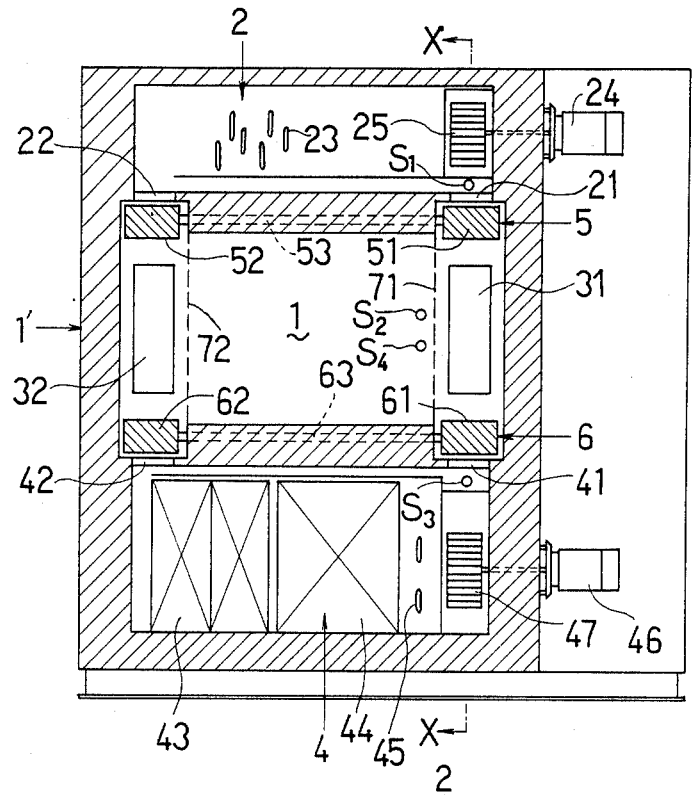
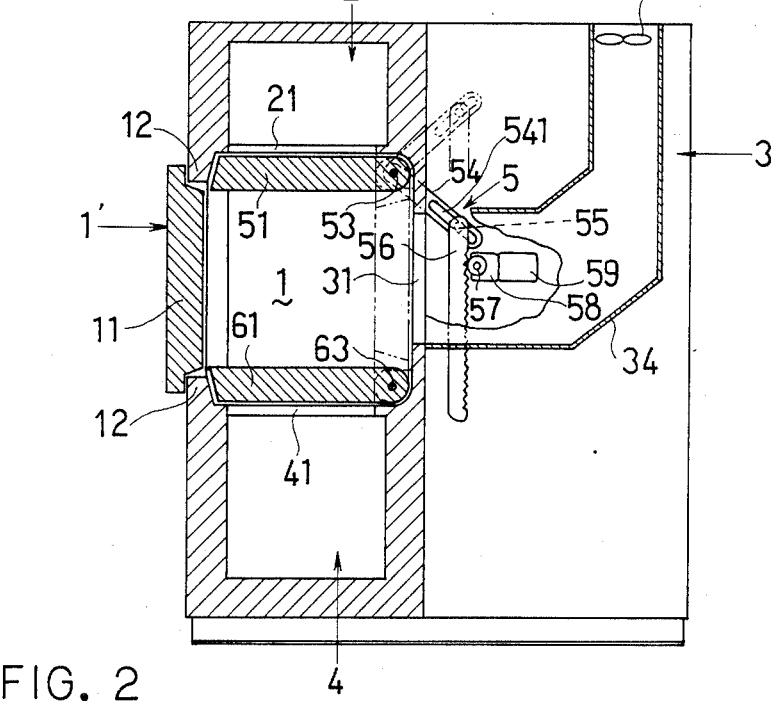
FIG. 1
FIG. 2

THERMAL SHOCK CHAMBER

This invention relates to a thermal shock chamber for testing various materials, parts of various devices or the like for thermal stress characteristics, durability, thermal strength, etc., for example, by exposing the test sample alternately to two of high-temperature, low-temperature and ambient-temperature atmospheres or successively to these atmospheres in a predetermined order.

Such chambers heretofore known include one comprising a test area for the test sample, a high-temperature air conditioning unit having gas outlet and intake adapted to communicate with the test area, an outside air supplying unit having air outlet and inlet adapted to communicate with the test area, and a low-temperature air conditioning unit having gas outlet and intake adapted to communicate with the test area. The thermal shock chamber of this type is provided with three dampers, i.e., one for opening or closing the gas outlet and intake of the high-temperature air conditioning unit, another for the air outlet and inlet of the outside air supplying unit, and another for the gas outlet and intake of the low-temperature air conditioning unit.

However, because the chamber is provided with these three dampers, the chamber is large-sized in its entirety, complicated in construction, costly to make and low in reliability in assuring safety and proper operation.

An object of the present invention is to provide a thermal shock chamber wherein a high-temperature air conditioning unit, low-temperature air conditioning unit and outside air supplying unit are brought into or out of communication with the test area by two damper means and which can be thereby made correspondingly smaller in its entirety, simpler, less costly and more reliable to operate.

The object of the invention can be fulfilled by a thermal shock chamber comprising a test area, a high-temperature air conditioning unit having a gas outlet and a gas inlet adjacent to the test area, an outside air supplying unit having an air outlet and an air inlet adjacent to the test area and to the gas outlet and inlet of the high-temperature air conditioning unit, a low-temperature air conditioning unit having a gas outlet and a gas inlet adjacent to the test area and to the air outlet and inlet of the outside air supplying unit, a first damper assembly for opening the outlet and the inlet of one of the high-temperature air conditioning unit and the outside air supplying unit and closing the outlet and the inlet of the other unit at the same time, and a second damper assembly for opening the outlet and the inlet of one of the low-temperature air conditioning unit and the outside air supplying unit and closing the outlet and the inlet of the other unit at the same time.

More specifically, a first damper assembly is movable between two end positions and to intermediate positions therebetween. At one of these end positions, the first damper assembly closes both the gas outlet and the gas inlet of the high temperature air conditioning unit while opening both the air outlet and the air inlet of the outside air supplying unit. At the other end position, the first damper assembly opens both the gas outlet and the gas inlet of the high temperature air conditioning unit while closing both the air outlet and the air inlet of the outside air supplying unit. A second damper assembly is also movable between two end positions and intermediate positions therebetween. At one of these end positions, the second damper closes both the gas outlet and the gas inlet of the low temperature air conditioning unit while opening both the air outlet and the air inlet of the outside air supplying unit. At the other end position, the second damper assembly opens both the gas outlet and the gas inlet of the low temperature air conditioning unit and closes both the air outlet and the air inlet of the outside air supplying unit.

According to a preferred embodiment of the invention there is provided a thermal shock chamber of the type described wherein one of the high-temperature air conditioning unit and the low-temperature air conditioning unit is provided immediately above the test area, and the other unit is provided immediately below the test area, the outside air supplying unit being provided close to the test area in the rear thereof, the gas outlets of the high-temperature and low-temperature air conditioning units being positioned above and below one side portion of the test area to communicate with the interior of the test area, the gas inlets of the high-temperature and the low-temperature air conditioning units being positioned above and below the other side portion of the test area to communicate with the interior of the test area, the gas outlets and the gas inlets extending substantially horizontally in the direction of the depth of the test area, the air outlet of the outside air supplying unit being positioned in the rear of said one side portion of the test area to communicate with the interior of the test area and extending substantially vertically in proximity to the gas outlets of the two air conditioning units, the air inlet of the outside air supplying unit being positioned in the rear of said other side portion of the test area to communicate with the interior of the test area and extending substantially vertically in proximity to the gas inlets of the two air conditioning units, the first damper assembly including a pair of dampers each pivotally movable about one end thereof to open the outlet and the inlet of one of the high-temperature air conditioning unit and the outside air supplying unit and to close the outlet and the inlet of the other unit at the same time, the second damper assembly including a pair of dampers each pivotally movable about one end thereof to open the outlet and the inlet of one of the low-temperature air conditioning unit and the outside air supplying unit and to close the outlet and the inlet of the other unit at the same time.

Preferably, the thermal shock chamber has a structure wherein each of the test area and the high-temperature air conditioning unit is provided with a temperature sensor for controlling the temperature of a hot gas, and each of the test area and the low-temperature air conditioning unit is provided with a temperature sensor for controlling the temperature of a cold gas, each of the temperature sensors for the hot gas being alternatively usable so that the sensor of the high-temperature air conditioning unit operates when this unit is in a closed-off standby state or the sensor of the test area for the hot gas operates when the test area is exposed to a high temperature by the high-temperature air conditioning unit, each of the temperature sensors for the cold gas being alternatively usable so that the sensor of the low-temperature air conditioning unit operates when this unit is in a closed-off standby state or the sensor of the test area for the cold gas operates when the test area is exposed to a low temperature by the low-temperature air conditioning unit.

The temperature sensors thus arranged make it possible to control the temperature of the atmosphere within the air conditioning unit in the closed-off standby state in preparation for the subsequent heat cycle and to control the high-temperature or low-temperature atmosphere of the test area. Consequently the test sample in the test area can be subjected to a thermal shock test properly with high accuracy.

The above and other objects, features and advantages of the invention will become apparent from the following description of the invention with reference to the accompanying drawings which are given for illustrative purposes only and to which the invention is not limited. In these drawings:

FIG. 1 is a view schematically showing a thermal shock chamber according to one embodiment of the present invention and in section taken in parallel with its door at a position a small distance away from the door toward the rear; and FIG. 2 is a view in section taken along the line X—X in FIG. 1 and schematically showing the chamber with the interior components of air conditioning units omitted.

The thermal shock chamber illustrated in the drawings comprises a casing 1' providing a test area 1, and a high-temperature air conditioning unit 2, an outside air supplying unit 3 and a low-temperature air conditioning unit 4 adjacent the test area 1 and disposed immediately above, behind and below the test area 1, respectively.

The casing 1' has an openable door 11 for entirely closing the front ide of the test area 1. Although the drawings show a clearance between the door 11 and a front portion 12 of the casing 1', the clearance is of course sealed off substantially hermetically by suitable known means when the door 11 is closed.

The high-temperature air conditioning unit 2 has a gas outlet 21 and a gas inlet (intake) 22 which are positioned above opposite side portions of the test area. 1 to communicate with the area 1. Air is heated by a heater 23 and then supplied to the test area 1 from the outlet 21 by a fan 25 driven by a motor 24. The air in the test area 1 is drawn into the unit 2 through the inlet 22. Thus hot air is circulated through the test area 1.

The outside air supplying unit 3 has an air outlet 31 and an air inlet (vent) 32 which are positioned in the area of the opposite side portions of the test area 1 to communicate with the test area 1. By a fan 33 driven by an unillustrated motor, outside air in the vicinity of the test chamber is supplied to the test area 1 through a duct 34 and the outlet 31 and is then forced out from the test area through the inlet 32 of the unit 3.

The gas outlet 21 and the air outlet 31 are adjacent to each other. The outlet 21 extends substantially horizontally in the direction of the depth of the casing 1', while the air outlet 31 extends substantially vertically. The gas inlet 22 and the air inlet 32 are also adjacent to each other. The inlet 22 extends substantially horizontally in the direction of the depth of the casing 1', while the air inlet 32 extends substantially vertically.

The low-temperature air conditioning unit 4 has a gas outlet 41 and a gas inlet (intake) 42 which are positioned below the opposite side portions of the test area 1 to communicate with the area 1. The unit 4 comprises a cold accumulator 43, an evaporator 44, a temperature control heater 45, etc. By a fan 47 driven by a motor 46, the cold air produced is supplied to the test area 1 through the outlet 41, and the air in the test area 1 is drawn into the unit 4 via the inlet 42. Thus, cold air is circulated through the test area.

The cold air outlet 41 is adjacent to the outside air outlet 31 and extends substantially horizontally in the direction of the depth of the casing 1'.

The cold air inlet 42 is adjacent to the outside air inlet 32 and similarly extends substantially horizontally in the direction of the depth of the casing 1'.

Damper assemblies are indicated at 5 and 6 in the drawings. The damper assembly 5 comprises dampers 51 and 52 which are fixed to opposite ends of a rod 53. The rod 53 is rotatably supported at the upper rear corner of the casing 1'. The dampers 51 and 52 are pivotally movable upward and downward at the same time by the rotation of the rod 53. When in their raised position, these dampers close the outlet 21 and inlet 22 of the air conditioning unit 2, while when in their lowered position, the dampers close the outlet 31 and inlet 32 of the outside air supplying unit 3.

An arm 54 having a slot 541 is fixed approximately to the midportion of the rod 53. The arm 54 extends through a vertical slit (not shown) formed in the rear wall of the casing 1' to project from the casing 1' rearward. A horizontal pin 55 slidably fitted in the slot 541 of the arm 54 is fixed to the upper end of a vertical rack 56 which is vertically movably supported by an unillustrated frame. The rack 56 is movable upward and downward by a motor 59 through a pinion 57 meshing with the rack and a suitable reduction gear 58. The reduction gear 58 and the motor 59 are also supported by the unillustrated frame. Thus the dampers 51 and 52 are pivotally movable upward and downward by the vertical movement of the pin 55 at the upper end of the rack effected by the motor 59, pivotal movement of the arm 54 by the vertical movement of the pin and rotation of the rod 53 effected by the pivotal movement of the arm.

The damper assembly 6 comprises dampers 61 and 62 which are fixed to opposite ends of a rod 63. The rod 63 is rotatably supported at the lower rear corner of the casing 1'. The dampers 61 and 62 are pivotally movable upward and downward at the same time by the rotation of the rod 63. When in their raised position, the dampers close the outlet 31 and inlet 32 of the outside air supplying unit 3, while when in their lowered position, the dampers close the outlet 41 and inlet 42 of the air conditioning unit 4.

The rod 63 is provided with drive means (not shown) which is substantially the same as the one provided for the rod 53 of the damper assembly 5. The dampers 61 and 62 are pivotally movable upward and downward by the rotation of the rod 63 effected by its drive means.

Although there is a clearance between the dampers 51, 52 in the solid-line position illustrated and the opening portions 21, 22 of the high-temperature air conditioning unit 2, between the dampers 61, 62 in the illustrated solid-line position and the opening portions 41, 42 of the low-temperature air conditioning unit 4, and between the dampers in the phantom-line position shown in FIG. 2 and the outside air outlet 31 and inlet 32, such clearances are of course sealed off substantially hermetically by suitable known means.

A temperature sensor S1 is disposed within the high-temperature air conditioning unit 2 in the vicinity of its outlet 1, while another temperature sensor S2 is disposed in the test area 1.

These sensors S1 and S2, which are, for example, thermocouples, etc., are adapted to control the temperature of a hot gas and are connected via unillustrated suitable change-over means to a single temperature controller for high temperatures.

Each of the sensors S1 and S2 is alternatively made usable by the change-over means, such that the sensor S1 of the high-temperature air conditioning unit 2 operates when this unit 2 is closed off from the test area 1 by the dampers 51 and 52 or the sensor S2 operates when the test area 1 is in communication with the unit 2 to conduct a high-temperature exposure test. The change-over means comprises suitable known means (such as a relay circuit or a switch mechanically coupled to the dampers).

A temperature sensor S3 is disposed within the low-temperature air conditioning unit 4 in the vicinity of its outlet 41, while another temperature sensor S4 is disposed in the test area 1.

The sensors S3 and S4, which are, for example, thermocouples, etc., are adapted to control the temperature of a cold gas and are connected via unillustrated suitable change-over means to a single temperature controller for low temperatures.

Each of the sensors S3 and S4 is alternatively made usable by the change-over means, such that the sensor S3 operates when the low-temperature air conditioning unit 4 is closed off from the test area 1 by the dampers 61 and 62 or the sensor S4 operates when the test area 1 is in communication with the unit 4 for a low-temperature exposure test. The change-over means also comprises known suitable means.

Indicated at 71 and 72 are perforated flow control panels to subject the test sample placed in the test area 1 to a uniform flow of air.

The sample to be tested is placed in the test area 1 between the two flow control panels 71 and 72.

For a high-temperature exposure test, the dampers 51 and 52 of the damper assembly 5 are held in their lowered position to open the outlet 21 and inlet 22 of the high-temperature air conditioning unit 2, with the outlet 31 and inlet 32 of the outside air supplying unit 3 closed, the dampers 61 and 62 of the damper assembly 6 are held in their lowered position to close the outlet 41 and inlet 42 of the low-temperature air conditioning unit 4, and the sample in the test area 1 is exposed to a high temperature for a predetermined period of time.

For a low-temperature exposure test, the dampers 51 and 52 are held in their raised position to close the outlet 21 and inlet 22 of the air conditioning unit 2, the dampers 61 and 62 of the damper assembly 6 are held in their raised position to open the outlet 41 and inlet 42 of the air conditioning unit 4, with the outside air outlet 31 and inlet 32 closed, and the sample in the test area 1 is exposed to a low temperature for a specified period of time.

Further when it is desired to conduct a room-temperature exposure test, the dampers 51 and 52 are held in their raised position to close the outlet 21 and inlet 22 of the unit 2, the dampers 61 and 62 are held in their lowered position to close the outlet 41 and inlet 42 of the unit 4, with the outlet 31 and inlet 32 of the outside air supplying unit 3 opened, and the sample in the test area 1 is exposed for a specified period of time to the air admitted thereinto from the neighborhood of the test chamber. During the high-temperature exposure test, the temperature of the test area 1 is controlled by the sensor S2 and unillustrated temperature controller for high temperatures.

During the low-temperature or room-temperature exposure test, the high-temperature air conditioning unit 2 is held in operation, ready for the next cycle of high-temperature exposure test, with the internal temperature of the unit 2 under the control of the sensor S1 and the aforementioned high temperature controller (not shown).

During the low-temperature exposure test, the temperature of the test area 1 is controlled by the sensor S4 and the low temperature controller (not shown).

During the high-temperature or room-temperature exposure test, the low-temperature air conditioning unit 4 is held in operation, ready for the next cycle of low-temperature exposure test, with the internal temperature of the unit 4 controlled by the sensor S3 and the aforementioned low temperature controller.

The foregoing is a description of preferred embodiment of the invention, and it will be understood that various modifications may be made without departing from the spirit of the invention or the scope of the appended claims.

We claim:

1. A thermal shock chamber comprising a test area, a high-temperature air conditioning unit having a gas outlet and a gas inlet adjacent to the test area, an outside air supplying unit having an air outlet and an air inlet adjacent to the test area and to the gas outlet and inlet of the high-temperature air conditioning unit, a low-temperature air conditioning unit having a gas outlet and a gas inlet adjacent to the test area and to the air outlet and inlet of the outside air supplying unit, a first damper assembly, means for moving the first damper assembly between two end positions and to positions between said end positions, at one of said end positions the first damper assembly closing both the gas outlet and gas inlet of the high-temperature air conditioning unit while opening both the air outlet and air inlet of the outside air supplying unit, and at the other of said end positions the first damper assembly opening both the gas outlet and the gas inlet of the high temperature air conditioning unit while closing both the air outlet and the air inlet of the outside air supplying unit, a second damper assembly, means for moving the second damper assembly between two end positions and to positions between said end positions, at one of said end positions the second damper assembly closing both the gas outlet and gas inlet of the low-temperature air conditioning unit while opening both the air outlet and air inlet of the outside air supplying unit, and at the other of said end positions the second damper assembly opening both the gas outlet and the gas inlet of the low temperature air conditioning unit while closing both the air outlet and the air inlet of the outside air supplying unit.

2. A chamber a defined in claim 1, said chamber having a front, a rear, one side portion and an other side portion, said test area having an interior defined by said front, rear, one side portion and said other side portion, and wherein one of the high-temperature air conditioning unit and the low-temperature air conditioning unit is provided immediately above the test area, and the other of said high-temperature air conditioning unit and the low-temperature air conditioning unit is provided immediately below the test area, the outside air supplying unit being provided close to the test area at said rear thereof, the gas outlets of the high-temperature and low-temperature air conditioning units being positioned above and below said one side portion of the test area to communicate with the said interior of the test area, the gas inlets of the high-temperature and the low-temperature air conditioning units being positioned above and below the said other side portion of the test area to communicate with the said interior of the test area, the gas outlets and the gas inlets extending substantially horizontally in the direction of the depth of the test area, the air outlet of the outside air supplying unit being positioned at said rear of said one side portion of the test area to communicate with the interior of the test area and extending substantially vertically in proximity to the gas outlets of the two air conditioning units, the air inlet of the outside air supplying unit being positioned at said rear of said other side portion of the test area to communicate with the interior of the test area and extending substantially vertically in proximity to the gas inlets of the two air conditioning units, the first damper assembly including a pair of dampers each pivotally movable about one end thereof to open the outlet and the inlet of one of the high-temperature air conditioning unit and the outside air supplying unit and to close the outlet and the inlet of the other of said high-temperature air conditioning unit and outside air supplying unit at the same time, the second damper assembly including a pair of dampers each pivotally movable about one end thereof to open the outlet and the inlet of one of the low-temperature air conditioning unit and the outside air supplying unit and to close the outlet and the inlet of the other of said low-temperature air conditioning unit and outside air supplying unit at the same time.

3. A chamber as defined in claim 1 wherein each of the test area and the high-temperature air conditioning unit is provided with a temperature sensor for controlling the temperature of a hot gas, and each of the test area and the low-temperature air conditioning unit is provided with a temperature sensor for controlling the temperature of a cold gas, each of the temperature sensors for the hot gas being alternatively usable so that the sensor of the high-temperature air conditioning unit operates when this unit is in a closed-off standby state or the sensor of the test area for the hot gas operates when the test area is exposed to a high temperature by the high-temperature air conditioning unit, each of the temperature sensors for the cold gas being alternatively usable so that the sensor of the low-temperature air conditioning unit operates when this unit is in a closed-off standby state or the sensor of the test area for the cold gas operates when the test area is exposed to a low temperature by the low-temperature air conditioning unit.

4. A chamber as defined in claim 2 wherein each of the test area and the high-temperature air conditioning unit is provided with a temperature sensor for controlling the temperature of a hot gas, and each of the test area and the low-temperature air conditioning unit is provided with a temperature sensor for controlling the temperature of a cold gas, each of the temperature sensors for the hot gas being alternatively usable so that the sensor of the high-temperature air conditioning unit operates when this unit is in a closed-off standby state or the sensor of the test area for the hot gas operates when the test area is exposed to a high temperature by the high-temperature air conditioning unit, each of the temperature sensors for the cold gas being alternatively usable so that the sensor of the low-temperature air conditioning unit operates when this unit is in a closed-off standby state or the sensor of the test area for the cold gas operates when the test area is exposed to a low temperature by the low-temperature air conditioning unit.

* * * * *